United States Patent [19]

Aoki et al.

[11] 4,299,455
[45] Nov. 10, 1981

[54] VISION TESTING INSTRUMENT

[75] Inventors: Mitsugu Aoki; Yoshinori Oana; Yasuo Kato; Taketoshi Ishihara, all of Tokyo, Japan

[73] Assignee: Tokyo Kogaku Kikai Kabushiki Kaisha, Tokyo, Japan

[21] Appl. No.: 142,230

[22] Filed: Apr. 21, 1980

[30] Foreign Application Priority Data

Apr. 27, 1979 [JP] Japan .................................. 54-52242

[51] Int. Cl.³ .............................................. A61B 3/02
[52] U.S. Cl. ........................................ 351/30; 351/27
[58] Field of Search ....................... 351/30, 26, 27, 28, 351/29, 17; 353/99, 101

[56] References Cited

U.S. PATENT DOCUMENTS 4,179,196 12/1979 Persson ................................. 351/30

Primary Examiner—John K. Corbin
Assistant Examiner—Rodney B. Bovernick
Attorney, Agent, or Firm—Brumbaugh, Graves, Donohue & Raymond

[57] ABSTRACT

A vision testing instrument has a projecting optical system for projecting a test chart to produce an aerial image. In the optical system, there is provided a focusing reflector for producing a chart image at a far point. A second focusing reflector is provided so that it can be retractably inserted into the projecting optical path for producing a chart image at a near point.

9 Claims, 2 Drawing Figures

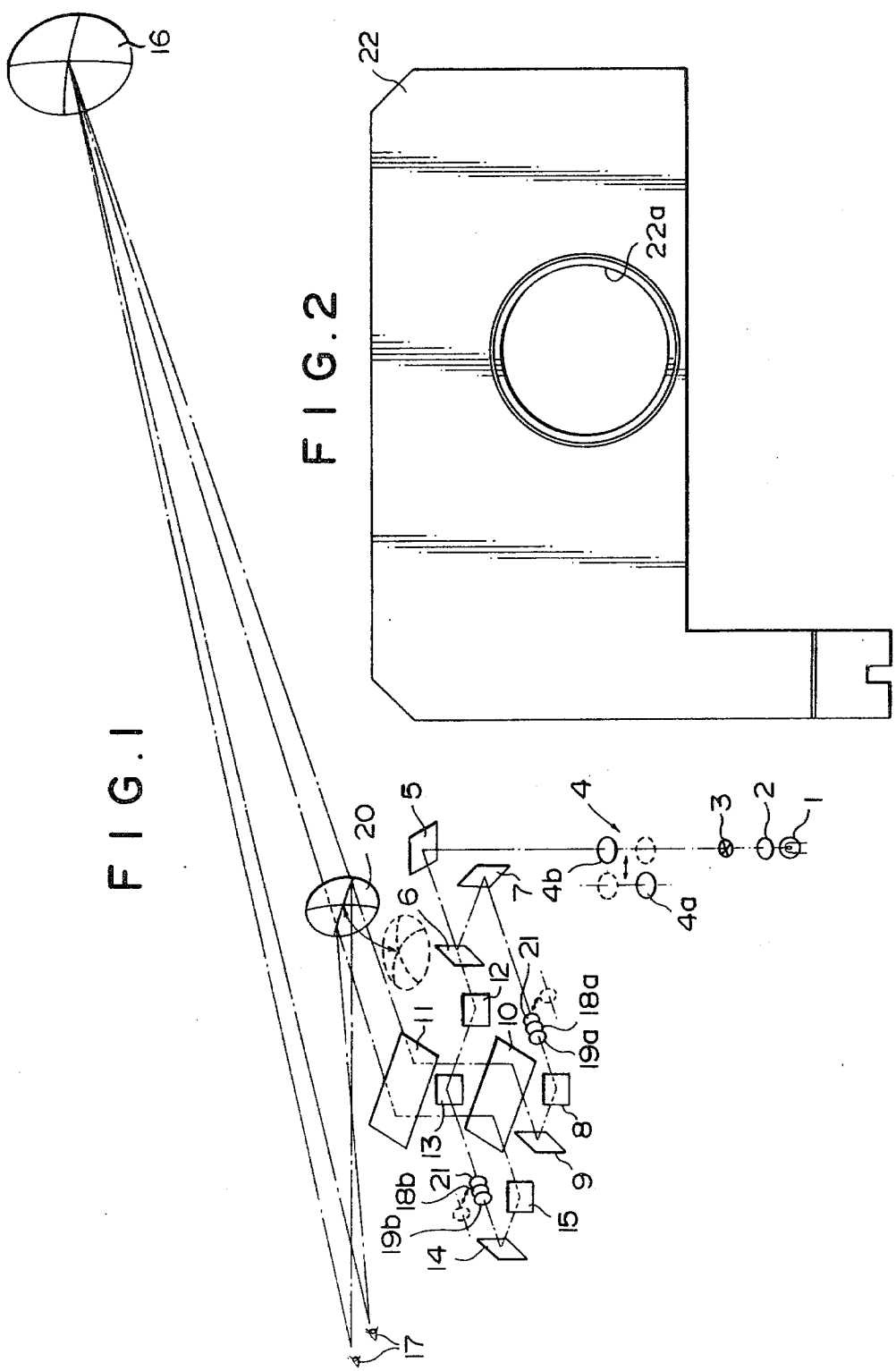

VISION TESTING INSTRUMENT

The present invention relates to vision testing instruments and more particularly to such instruments wherein test charts are projected through vision correcting lenses to produce aerial images of the charts so that patients can observe such images directly.

Conventionally, in this type of vision testing instruments, in order to make it possible to carry out near point view tests, a prism is inserted in front of the patient's eyes so that the patient's viewing lines are directed to an imaginary near point. In this type of arrangements, however, inconveniences have been encountered in that patients may sometimes fail to align their viewing lines to such imaginary near points or, even when they have once succeeded to get such alignments, the alignments may easily be lost due to possible slight fluctuations of the patient's consciousness. It should further be noted that, although one of the features of this type of vision testing instruments is that there is no obstacle in front of the patient's eyes, the aforementioned conventional arrangement requires a prism to be placed just in front of the patient's eyes.

It is therefore an object of the present invention to provide a vision testing instrument which does not require anything to be placed in front of the patient's eyes both in far point view test and in near point view test.

Another object of the present invention is to provide a vision testing instrument which includes means for preventing any change of visual angle of the test chart between a far and near point view tests.

A further object of the present invention is to provide a vision testing instrument which has means for assisting the patient to catch the projected chart image in a near point view test.

According to the present invention, the above and other objects can be accomplished by a vision testing instrument comprising a light source, a chart projecting optical system for projecting a testing chart, first focusing reflective means provided in said chart projecting optical system for producing a chart image at a far point for a far point view test, second focusing reflective means retractably positioned in said chart projecting optical system between said light source and said first focusing reflective means for producing a chart image at a near point, lens means adapted to be inserted into said chart projecting optical system when said second focusing reflective means is in said chart projecting optical system so that the chart image is focused at said near point, said lens means being adapted to be retracted when said second focusing reflective means is retracted from the chart projecting optical system. The first and second focusing reflective means may be in the forms of concave reflectors. Alternatively, combinations of lenses and planar reflectors may alsio be used. In order to prevent the visual angle of the projected chart image be changed between the far point and near point view tests, the chart projecting optical system may have projecting lens means of different focal lengths which may alternately be inserted into the system. Alternatively, test charts of different sizes may be provided for alternate use between the far point and near point view tests. In order for assisting the patient to catch the projected image in the near point view test, a reference plate may be retractably inserted into the chart projecting optical system at or in the vicinity of the projected image in the near point view test. In this instance, the plate may be interconnected with the second focusing reflective means so that the former can be inserted into the chart projecting optical system together with the latter.

The above and other objects and features of the present invention will become apparent from the following descriptions of preferred embodiment taking reference to the accompanying drawings, in which;

FIG. 1 is a diagrammatical perspective view of the optical system of a vision testing instrument in accordance with one embodiment of the present invention; and, FIG. 2 is a front view of a reference plate which may be adopted in the instrument shown in FIG. 1.

Referring now to the drawings, particularly to FIG. 1, the vision testing instrument shown therein includes a light source 1 from which light is projected through a diffusing disc 2 and a test chart 3 to a projecting optical path. In the projecting optical, there is provided a projecting lens 4 and the test chart 3 is projected through the lens 4 and reflected by a mirror 5 to a half-transparent mirror 6. The half-transparent mirror 6 functions to reflect a portion of the light bundle from the mirror and allows the remainder of the light bundle to pass therethrough. The light bundle reflected at the half-transparent mirror 6 is repeatedly reflected at mirrors 7, 8 and 9 to a common reflector 10 to be reflected thereby toward a common reflector 11 which reflect the light bundle forwardly. The light bundle which has passed through the half-transparent mirror 6 is reflected at mirrors 12, 13, 14 and 15 toward the common reflector 10. The light bundle is then further reflected at the mirror 11 forwardly.

The light bundles from the reflector 11 are then reflected by a concave reflector 16 having a concave spherical reflecting surface to produce an aerial image at a far point from patient's eyes 17. Between the mirrors 7 and 8, there is inserted a corrective cylindrical lens 18a and a corrective spherical lens 19a. Similarly, a corrective cylindrical lens 18b and a corrective spherical lens 19b are inserted between the mirrors 13 and 14. In order for near point view test, a second concave reflector 20 having a concave spherical reflecting surface is provided so that it can be retracted from the operative position shown by solid lines in FIG. 1 to a retracted position shown by broken lines. When the reflector 20 is inserted into the projecting optical path as shown by the solid lines in FIG. 1, the light bundle from the reflector 11 is reflected by the reflector 20 to produce a chart image at a near point to the eyes 17. In order to focus the chart image at the near point, lenses 21 are provided so that they are retractably inserted into the projecting paths in the vicinity of the corrective lenses simultaneously with the reflector 20.

In order to prevent the size of the projected image from being changed between the near point and far point view tests, the projecting lens 4 may be comprised of lenses 4a and 4b of different focal lengths so that they are alternately inserted into the projecting optical path depending on whether the reflector 20 is in the projecting optical path or not. Alternatively, test charts of different sizes may be provided for alternate insertion into the projecting optical path.

For the purpose of assisting the patient in catching the aerial chart image at the near point, it will be convenient to provide a reference plate 22 as shown in FIG. 2. The plate 22 is formed with an opening 22a and retractably inserted into the projecting optical path when the near point view test is being made, so that the chart image is produced in the opening 22a. With this arrangement, the patient naturally tend to watch the plate 22 so that he will readily catch the chart image. It is of course preferable that the plate 22 is interconnected with the reflector 20 so that the former is inserted into the optical path together with the latter.

The invention has thus been shown and described with reference to a specific embodiment, however, it should be noted that the invention is in no way limited to the details of the illustrated arrangement but changes and modifications may be made without departing from the scope of the appended claims.

We claim:

1. A vision testing instrument comprising a light source, a chart projecting optical system for projecting a testing chart, first focusing reflective means provided in said chart projecting optical system for producing a chart image at a far point for a far point view test, second focusing reflective means retractably positioned in said chart projecting optical system between said light source and said first focusing reflective means for producing a chart image at a near point, lens means adapted to be inserted into said chart projecting optical system when said second focusing reflective means is in said chart projecting optical system so that the chart image is focused at said near point, said lens means being adapted to be retracted when said second focusing reflective means is retracted from the chart projecting optical system.

2. A vision testing instrument in accordance with claim 1 in which said first and second focusing reflective means are concave reflectors.

3. A vision testing instrument in accordance with claim 1 in which said first and second focusing reflective means are combinations of lenses and planar reflectors.

4. A vision testing instrument in accordance with claim 1 which further includes optical means for preventing change in size of the chart images at the far and near points.

5. A vision testing instrument in accordance with claim 4 in which said optical means for preventing the change in size of the chart images comprises means for alternately inserting projecting lenses of different focal distances into projecting optical path.

6. A vision testing instrument in accordance with claim 4 in which said optical means for preventing the change in size of the chart images comprises test charts of different sizes which are adapted to be alternately inserted into projecting optical path depending on whether a far point view test or a near point view test is to be carried out.

7. A vision testing instrument in accordance with claim 1 in which reference means is provided for retractable insertion into optical path in the vicinity of the chart image at the near point when the second focusing reflective means is in the optical path.

8. A vision testing instrument in accordance with claim 7 in which said reference means is interconnected with the second focusing reflective means so that the former is inserted into the optical path together with the latter.

9. A vision testing instrument in accordance with claim 1 in which said reference means comprises a plate formed with an opening where the chart image at the near point is produced.

* * * * *